United States Patent [19]

Hu et al.

[11] 4,307,245

[45] Dec. 22, 1981

[54] AMITRIPTYLINE CONJUGATES TO ANTIGENIC PROTEINS AND ENZYMES

[75] Inventors: Mae W. Hu, Sunnyvale; Prithipal Singh, Santa Clara, both of Calif.

[73] Assignee: Syva Company, Palo Alto, Calif.

[21] Appl. No.: 137,658

[22] Filed: Apr. 7, 1980

Related U.S. Application Data

[62] Division of Ser. No. 974,294, Dec. 29, 1978, Pat. No. 4,223,013.

[51] Int. Cl.$^3$ .................. C07C 87/459; C07C 101/28; C07C 101/34
[52] U.S. Cl. ...................................... 562/442; 560/37; 564/380; 260/326.4; 424/12
[58] Field of Search .......................... 562/442; 560/37; 564/37

[56] References Cited

U.S. PATENT DOCUMENTS

| | | | |
|---|---|---|---|
| 3,234,279 | 2/1966 | Kollonitsch et al. | 564/380 |
| 3,309,404 | 3/1967 | Engelhardt | 564/380 |
| 3,324,170 | 6/1967 | Kollonitsch | 564/380 |
| 3,372,196 | 3/1968 | Engelhardt | 560/37 |
| 3,379,750 | 4/1968 | Kollonitsch | 562/442 |
| 3,445,519 | 5/1969 | Kollonitsch | 560/37 |
| 3,818,020 | 6/1974 | Huebner | 560/37 |
| 3,981,917 | 9/1976 | Engelhardt | 560/37 |

*Primary Examiner*—Natalie Trousof
*Assistant Examiner*—James H. Reamer
*Attorney, Agent, or Firm*—Bertram I. Rowland

[57] ABSTRACT

Amitriptyline functionalized compounds are provided for conjugation to antigenic compositions, particularly poly(amino acids), and enzymes. The antigenic conjugates are employed for the production of antibodies, which find particular use in immunoassays for the determination of amitriptyline, while the enzyme conjugate finds use in a homogeneous enzyme immunoassay for the determination of amitriptyline.

6 Claims, No Drawings

AMITRIPTYLINE CONJUGATES TO ANTIGENIC PROTEINS AND ENZYMES

This is a division of application Ser. No. 974,294 filed Dec. 29, 1978, now U.S. Pat. No. 4,223,013.

BACKGROUND OF THE INVENTIONS

1. Field of the Invention

Amitriptyline is a tricyclic antidepressant which finds extensive use. The therapeutic range for the drug is from about 50 to 175 ng/ml. Lower dosages do not have significant effect and overdosages have substantial side effects which can be life-threatening. Overdoses can be characterized by convulsions, coma, cardiac arrhythmias, and anticholinergic signs, such as mydriasis and tachycardia.

It is found that the rate of metabolism of the drug can vary widely with individuals, as well as the sensitivity of the individual to the drug. It is therefore necessary to insure proper dosage levels to monitor the plasma level, so that a therapeutic dosage level may be maintained.

In monitoring the dosage level, it is desirable that there be a simple accurate rapid technique for measuring the amitriptyline level, which can distinguish amitriptyline from other drugs and metabolites of amitriptyline, which might otherwise give an erroneous value of the amitriptyline level.

2. Brief Description of the Prior Art

Techniques reported for the determination of amitriptyline in biological fluids include the use of thin-layer chromatography, gas-liquid chromatography and GLC-mass spectrometry. Gifford, et al., *J. of Chrom.*, 105, 107–113 (1975); Gupta, et al., *Clin. Biochem.*, 9, 247–51 (1976); Nyberg and Martensson, *J. Chromatography*, 143, 491 (1977); Watson and Stewart, *J. Chrom.*, 134, 182 (1977); ibid. 132 155–159 (1977). Radioimmunoassay has been reported for amitriptyline by Aherne, et al., *Br. J. Clin. Pharmac.*, 3, 561 (1976), Turner, *Lancet*, 180, 1316 (1977); and Aherne, et al., Lancet 1214 (1977). In Aherne, et al., ibid., a synthesis for an antigen for antibody formation is described, where nortriptyline is substituted with aminobutylene followed by conjugation to bovine serum albumin employing carbodiimide. In another antigen conjugate synthesis by Kaul, et al., *J. Anal. Tox.*, 1, 236 (1977), nortriptyline was conjugated to bovine serum albumin through a succinic group. The resulting antibodies were found to have significant cross-reactivity with a number of other tricyclic drugs.

SUMMARY OF THE INVENTION

A synthetic procedure is provided for preparing amitriptyline derivatives having an oxo functionality-containing substituent on an aryl ring for conjugation to antigenic materials, particularly poly(amino acids) and enzymes. The antigenic conjugate is employed for the production of antibodies for use in immunoassays. The enzyme conjugate is employed as a reagent for the determination of amitriptyline in immunoassays. The antibodies and enzyme conjugates are provided in combination in kits to be used for the rapid and accurate determination of amitriptyline in serum as well as other physiological fluids.

DESCRIPTION OF THE SPECIFIC EMBODIMENTS

Amitriptyline derivatives are provided having an oxo functionality containing substituent on an aryl ring for conjugation to poly(amino acids), which are antigenic or enzymes. The antigenic conjugates are employed for the production of antibodies which are specific for amitriptyline for use in immunoassays. The enzyme conjugates are employed as a reagent in a homogeneous enzyme immunoassay for the determination of amitriptyline.

For the most part, the compounds of this invention will have the following formula:

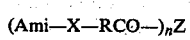

wherein:
Ami is of the formula

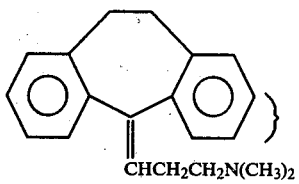

X is methylene or carbonyl;
R is a linking group, normally aliphatic hydrocarbon, of from 1 to 7, more usually of from 1 to 5 carbon atoms, and preferably of from 2 to 4 carbon atoms;
Z is hydroxyl, alkoxyl of from 1 to 6 carbon atoms, an activating oxy group to form an activated ester, e.g. N-oxy succinimide and p-nitrophenoxy, or a poly(amino acid), which is antigenic or an enzyme, which poly(amino acid) is joined by an amide bond;
n is 1 when Z is other than a poly(amino acid) and is otherwise 1 to the molecular weight of Z divided by 500, more usually divided by 1,000, and frequently divided by 1,500, generally ranging from about 1 to 500, preferably from about 10 to 100, when Z is an antigen, and from about 1 to 30, more usually from about 2 to 20, and preferably from about 2 to 16, when Z is an enzyme.

The linking group —XR—, with the X bonded to amitriptyline, and counting from amitriptyline, may be a 1-oxo aliphatic group having from 0 to 1 site of unsaturation, preferably ethylenic, and may be branched or straight chain, preferably straight chain, particularly polymethylene. Where the linking group is bound to other than a poly(amino acid), it may have 1-oxo or an alklyene or alkenylene group. However, with a poly(amino acid), the linking group will normally be hydrocarbon. If the linking group is branched chain, there will normally be not more than two branches, more usually not more than one branch of from one to two carbon atoms.

The preferred linking group will be derived from a cyclic anhydride, such as succinic anhydride, maleic anhydride, glutaric anhydride and azelaic anhydride, that is anhydrides forming rings of from 5 to 7 members. As such, the linking group will preferably be 1-oxopropylene, 1-oxobutylene, 1-oxopentylene, 1-oxomethylbutylene, 1-oxopropenylene, propylene, butylene, and 3-methylbutylene.

For those compounds where n is 1, the compounds will have the following formula:

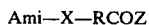

wherein all the symbols have been defined previously.

Where n is at least 1 and Z is a poly(amino acid), the compounds will for the most part have the following formula:

(Ami—CH$_2$—R$^1$CO)$_{n1}$Z$^1$ wherein:

Ami has been defined previously;

R$^1$ can be the same as R, but is preferably alkylene, particularly polymethylene, of from 2 to 4 carbon atoms, more preferably of from 2 to 3 carbon atoms;

n$^1$ is at least 1, usually greater than 1; when Z$^1$ is antigenic, n$^1$ will normally be at least 2, and not greater than the molecular weight of Z$^1$ divided by 500, usually not greater than the molecular weight of Z$^1$ divided by 1,000, and preferably not greater than the molecular weight of Z$^1$ divided by 1,500, generally ranging from about 2 to 500; when Z$^1$ is an enzyme, n$^1$ will be at least 1, usually not greater than 30, more usually in the range of about 2 to 20, and preferably in the range of about 2 to 16.

The poly(amino acids) will generally range from about 5,000 molecular weight, having no upper molecular weight limit, normally being not less than 10,000, usually not more than about 600,000. There will usually be different molecular weight ranges, depending on whether an antigen or an enzyme is involved, with antigens ranging from about 5,000 to 10$^7$, usually from about 20,000 to 600,000, and more usually from about 25,000 to 250,000 molecular weight; while enzymes will generally range from about 10,000 to 600,000, more usually from about 10,000 to 300,000 molecular weight. There will usually be at least about one conjugate per 500,000 molecular weight, more usually at least one per 50,000 molecular weight. With intermediate molecular weight antigens (35,000 to 1,000,000), the number of conjugate groups will generally be from about 2 to 250, more usually from 10 to 100. With lower molecular weight antigens, below 35,000, the number of conjugates will generally be in the range of from about 2 to 10, usually in the range of 2 to 5.

Various protein types may be employed as the antigenic material. These types include albumins, serum proteins, e.g., globulins, ocular lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups, e.g., lysines.

The enzymes can be varied widely, depending upon the rapidity with which one desires a result and the physiological fluid in which the amitriptyline is to be measured. Primarily, the enzymes of choice, based on the I.U.B. classification are: Class 1. Oxidoreductases and Class 3. Hydrolases. Particularly in Class 1, the enzymes of interest are dehydrogenases of Class 1.1, more particularly 1.1.1 and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the peroxidases, horse radish peroxidase is illustrative. Of the hydrolases, alkaline phosphatase, β-galactosidase, β-glucosidase and lysozyme are illustrative.

Particularly preferred are those enzymes which employ nicotinamide adenine dinucleotide (NAD) or its phosphate (NADP) as a cofactor, particularly the former. Most preferred as the choice of enzyme is glucose 6-phosphate dehydrogenase.

Desirably the conjugated enzyme will be at least 40% inhibited, usually at least about 60% inhibited when saturated with anti(amitriptyline) while the conjugate will be less than 80% deactivated, preferably less than 60% deactivated.

The synthetic scheme for preparing the subject compounds is set forth in the following flowchart:

CHART 1

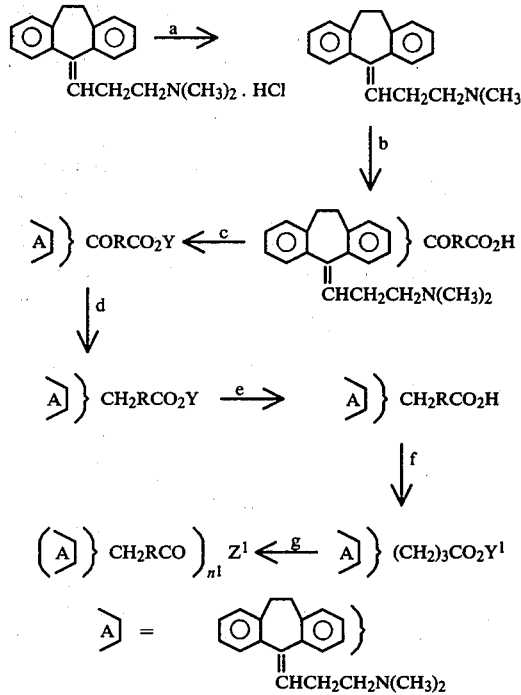

a OH$^\ominus$
b AlCl$_3$, CH$_2$Cl$_2$, R(CO)$_2$O
c YOH, H$^\oplus$
d Zn, HCl
e H$^\oplus$, THF
f Y$^1$OH, carbodiimide
g Z$^1$H, 0–10° C., pH-9

R, n$^1$ and Z$^1$ have been defined previously

Y is a lower alkanol of from 1 to 6, preferably 2 to 3 carbon atoms.

Y$^1$ is an hydroxy compound which forms an ester capable of amide formation with a poly(amino acid) in an aqueous medium.

In carrying out the preparation of the compositions of this invention, the amitriptyline-hydrochloride is carefully neutralized to provide the parent amine, followed by a Friedel-Crafts reaction under mild conditions employing aluminum chloride and a cyclic aliphatic anhydride to form the ω-carboxyalkyl arylketone, normally as a mixture at the 2 and 3 positions. The product may then be esterified with a lower alkanol under mild acidic conditions, followed by reduction of the oxo group to methylene with zinc and dry hydrogen chloride in an ethereal solvent. The carboxylic acid may then be employed to form an ester which reacts in an aqueous medium with amino groups of poly(amino acids) to form amide bonds. Illustrative hydroxylic groups include N-hydroxy succinimide and p-nitrophenol. The ester may be formed employing a carbodiimide to activate the carboxylic acid. The resulting ester may then be combined with the appropriate poly(amino acid) in an aqueous buffered medium with cooling and the pH maintained and monitored during the addition of the ester to the poly(amino acid).

By employing the above procedure, the amitriptyline is able to be functionalized to a compound which can be conjugated to poly(amino acids), either antigenic or enzymes. The structure of the amitriptyline is retained during the synthetic procedure and those elements of the structure which provide for distinctions between closely similar tricyclic antidepressants are exposed to allow for formation of antibodies which are capable of distinguishing amitriptyline from similarly structured compounds. The antigenic conjugates may be injected into a wide variety of vertebrates in accordance with conventional methods for the production of antibodies. Usually, the animals are bled periodically with the successive bleeds improving in titer and specificity and then plateauing and diminishing in their specificity and titer.

As previously indicated, the antibodies and enzyme reagents prepared in accordance with the subject invention find particular use in immunoassays for the determination of amitriptyline. A description of the method for carrying out the immunoassay, which is a homogeneous enzyme immunoassay, may be found in U.S. Pat. No. 3,817,837. The method involves combining the enzyme conjugate, the unknown sample suspected of containing amitriptyline, and an antibody for amitriptyline in an aqueous buffered medium at temperatures in the range of about 10° to 50°, more usually from about 20° to 40° C., and determining the enzyme activity as compared to the enzyme activity of an assay medium having a known amount of amitriptyline.

EXPERIMENTAL

The following examples are offered by way of illustration and not by way of limitation.

(All temperatures not otherwise indicated are in Centigrade. All percents not otherwise indicated are by weight. Parts are by weight, except when two liquids are combined and are then by volume.)

EXAMPLE 1

Preparation of Amitriptyline Free Base from Amitriptyline Hydrochloride

A solution of amitriptyline hydrochloride (10 g) in 15 ml of water was made basic with 5% NaHCO$_3$ (~100 ml), and then with 2 N NaOH (5 ml) (pH Hydroin paper 8~9). The resulting milky solution was extracted with chloroform and the chloroform extracts were dried over Na$_2$SO$_4$. Evaporation of solvent gave a light yellow oil which became viscous after being dried in vacuo as the amitriptyline free base (9.7 g).

EXAMPLE 2

Preparation of β-Amitriptyloylpropionic Acid

To a solution of amitriptyline (2.1 g, 7.58 mmoles) in dichloromethane (40 ml, distilled over CaH$_2$ and stored in molecular sieves 3A) was added powdered AlCl$_3$ (2.1 g, 15.7 mmoles, freshly opened bottle) under nitrogen at 0°. To the resulting red solution was then added succinic anhydride (758 mg, 7.58 mmoles), and the reaction mixture was stirred at 0° for 5–10 minutes and then at room temperature.

After 18 hours, a mixture of 1 NHCl (10 ml) and ice-water (20 ml) was added to the red reaction product and the residue became soluble after being stirred for about 0.5 hr. at 5°. The resulting two-phase yellow solution was evaporated on a rotary evaporator until the methylene chloride was removed completely. The yellow aqueous solution was then extracted exhaustively, using a mixture of tetrahydrofuran-ethyl acetate (a total of about 750 ml). The organic layer was then washed with a small amount of saturated aqueous NaCl and dried over Na$_2$SO$_4$. Evaporation of solvent gave a yellow gummy salt of β-(2- and 3-) amitriptyloylpropionic acid (3.0 g) after the product was dried in vacuo. While in this example, the product was homogeneous on tlc (one spot, Rf 0.20, 20% MeOH/CHCl$_3$, silica gel plate) and was esterified without further purification, in most cases unreacted starting material was present. To remove amitriptyline from the keto acid, the yellow gummy crude product was dissolved in water which was made basic with 15% NH$_4$OH to pH9, and the resulting aqueous solution extracted exhaustively with ether until the complete removal of amitriptyline from the aqueous solution. The aqueous phase was then acidified using 1 N HCl and evaporated to dryness. The keto acid which was free of amitriptyline was esterified directly without further purification.

EXAMPLE 3

Preparation of Ethyl 2- and 3-Amitriptyloyl Propionate (2- and 3-)Amitriptyloylpropionic acid (3.0 g Ex. 2) was refluxed in a mixture of ethanol (150 ml) and concentrated sulfuric acid (0.5 ml) for 3 hrs. The resulting solution was cooled (5°) and carefully made basic using 5% NaHCO$_3$ (about 40 ml). The solution was then extracted with chloroform and dried over Na$_2$SO$_4$. Evaporation of solvent gave a crude oily product of ethyl (2- and 3-)amitriptyloylpropionate (3.1 g).

The crude product (3.1 g) was purified on preparative tlc plates (20 plates, silical gel, solvent: CH$_2$Cl$_2$:i-PrOH:NH$_4$OH/60:40:0.2) to give 2.2 g of ethyl (2- and 3-)amitriptyloylpropionate.

For large scale preparation in a separate experiment, the crude product was purified on a column containing silica gel (5 g crude product, 200 g silica gel in CHCl$_3$, 45 cm × 34 cm) and eluted with 100 ml of CHCl$_3$, 500 ml of 5% MeOH/CHCl$_3$ and then 1 liter of 10% MeOH/CHCl$_3$. Total yield of ethyl (2- and 3-)amitriptyloylpropionate was 3.5 g. From this experiment, a small amount of 3-amitriptyloylpropionate (33 mg) was separated from the 2-isomer in the early fractions. However, the mixture of 2- and 3-isomers (3.0 g) was eluted in the later fractions, and the last fractions were collected and chromatographed on six tlc plates (silica gel plates, 20% MeOH/CHCl$_3$) to give 145 mg of pure 2-isomer.

The mixture of ethyl 2- and 3-amitriptyloylpropionate (150 mg) was dissolved in a minimum amount of chloroform, and the resulting solution was placed uniformly on nine preparative thick layer silica gel plates (2 mm) with a Chromaflex ® Streaker. The plates were developed at least twice in a solvent mixture of CH$_2$Cl$_2$:i-PrOH:NH$_4$OH/60:40:0.2. The resulting bands of Rf 0.75 and Rf 0.66 were recovered from 30% MeOH/CHCl$_3$. The sample of Rf of 0.75 (63.8 mg) was identified to be ethyl 3-amitriptyloylpropionate and that of Rf 0.66 (30.6 mg) was identified to be ethyl 2-amitriptyloylpropionate from nmr spectra.

EXAMPLE 4

Preparation of (2- and 3-) γ-Carbethoxypropylamitriptyline

Commercial zinc powder was washed well with 2% HCl for 4–5 minutes and the suspension filtered and the isolated zinc powder was then washed with water, ethyl alcohol, acetone and dry ether. The powder was dried overnight at reduced pressure at room temperature and then used.

A solution of cold (0°) ether (400 ml) saturated with HCl gas was added to ethyl (2- and 3-)amitriptyloylpropionate (3.5 g oily compound) which became soluble after being stirred. To the resulting clear solution was added at 0° freshly activated ZN (10 g) over a period of 15 minutes under nitrogen. The reaction mixture was stirred at 0° for 2 hours and a small aliquot was withdrawn, made basic with 5% NaHCO$_3$, and extracted with chloroform. The tlc of the chloroform extract showed complete reaction (silica gel plate 0.15:0.5:10/NH$_4$OH:MeOH:ether).

Excess ether-HCl was removed by evaporating the reaction product (two phase system) on a rotary evaporator (in a hood) and the resulting yellow oil carefully made basic using 5% NaHCO$_3$ at 5°–10°. The white solid (inorganic salt) was filtered and washed with ethyl acetate. The filtrate was then extracted with ethyl acetate and dried over Na$_2$SO$_4$. Evaporation of solvents gave 2.6 g light yellow oily product. The product gave 1.3 g (38.5% yield) of pure (2- and 3-) γ-carbethoxypropylamitriptyline after purification using either preparative tlc or column chromatography which are described below.

a. The crude reaction product (700 mg) was chromatographed on nine silica gel plates (10% MeOH/CHCl$_3$) and the band was recovered by eluting with 30% MeOH/CHCl$_3$ to yield 325 mg of (2- and 3-) γ-carbethoxypropylamitriptyline.

b. The crude reduction product (1.9 g) was chromatographed on a column containing silica gel (170 g in CHCl$_3$, 4.5 cm × 34 cm), eluted first with 50 ml CHCl$_3$, then with 200 ml 5% MeOH/CHCl$_3$, and then with 500 ml 10% MeOH/CHCl$_3$. After the fractions were combined, total yield of (2- and 3-) γ-carbethoxypropylamitriptyline from column chromatography was 942 mg.

c. The conditions were identical to those of the keto ester described in Example 3. The mixture was dissolved in a minimum amount of chloroform and the resulting solution was placed uniformly on preparative thick layer silica gel plates (2 mm, about 15–18 mg/plate) using a Chromaflex® Streaker. The plates were developed at least twice in a solvent mixture of CH$_2$Cl$_2$:i-PrOH:NH$_4$OH/60:40:0.2. The bands of Rf 0.74 and Rf 0.66 were recovered by eluting with 30% MeOH/CHCl$_3$. The crude reduction product (1.66 g) gave 333 mg pure 3-carbethoxypropylamitriptyline (Rf 0.74) and 138 mg 2-carbethoxypropylamitriptyline (Rf 0.66).

EXAMPLE 5a

Preparation of 3-Carboxypropylamitriptyline Hydrochloride

A solution of 3-carbethoxypropylamitriptyline (307 mg) in 4.6 ml of tetrahydrofuran was mixed with 4.6 ml of 18% hydrochloric acid at room temperature, and the light yellow solution was allowed to stand at room temperature under nitrogen.

After 18 hours, an aliquot was spotted on tlc and showed complete reaction (silica gel, 20% MeOH/CHCl$_3$, Rf 0.22). The resulting product was evaporated to dryness to give an oily foamy residue (290 mg) which showed only a small amount of impurity of Rf 0.59.

The product could be purified on four preparative thick layer plates (silica gel, 20% MeOH/CHCl$_3$) and the sample was recovered by eluting with large amounts of solvents (60% MeOH/CHCl$_3$, 1 liter). The resulting sample was redissolved in chloroform and filtered through glass wool to remove silica gel, and the filtrate evaporated to give a light yellow foaming residue (215 mg, yield 68.6%) of 3-(γ-carboxypropyl)amitriptyline hydrochloride.

EXAMPLE 5b

Preparation of 2- and 3-(γ-Carboxypropylamitriptyline Hydrochloride

A solution of 2- and 3-(γ-carboxypropyl)amitriptyline (325 mg) in 4.9 ml of tetrahydrofuran was mixed with 4.9 ml of 18% hydrochloric acid at room temperature, and the light yellow solution was allowed to stand at room temperature under nitrogen.

After 18 hours, an aliquot was spotted on tlc and showed complete reaction (silica gel, 20% MeOH/CHCl$_3$, Rf 0.29). The resulting product was evaporated to dryness to give an oily foamy residue which was purified on preparative thick layer plates (6 silica gel plates, 20% MeOH/CHCl$_3$). The sample was recovered by eluting with 60% MeOH/CHCl$_3$ (1 liter) and was then redissolved in CHCl$_3$ and filtered to remove silica gel. Evaporation of the filtrate gave a light yellow foamy residue (222 mg, 66.9% yield) of 2- and 3-(γ-carboxypropyl)amitriptyline hydrochloride.

EXAMPLE 6

Conjugation of 3-(γ-Carboxypropylamitriptyline to Carrier Proteins (381-142)

a. To 3-(γ-carboxypropyl)amitriptyline hydrochloride 94 mg, 0.236 mmole) in 1.89 ml of N,N-dimethylformamide (dried over molecular sieves 3A) was added triethylamine (32 μl), N-hydroxy succinimide (NHS, 32.5 mg, 0.282 mmole) and 1-ethyl-3(3-dimethylaminopropyl)carbodiimide HCl (EDAC, 53.8 mg, 0.282 mmole) at 5° under nitrogen. The reaction mixture was then allowed to stir in the cold room. After 18 hrs, the conversion to the NHS ester was observed on tlc (silica gel plate, Rf 0.65, 20% MeOH/CHCl$_3$).

b. The NHS ester of 3-(γ-carboxypropyl)amitriptyline (1.1 ml in DMF, from 51.7 mg acid, 0.130 mmole) was added dropwise at 0° to a solution of bovine serum albumin (BSA 250 mg, 0.221 mmole lysine) in a mixture of carbonate buffer (12.5 ml, pH9, 0.05 M) and N,N-dimethylformamide (3.5 ml) for a period of 0.5 hr. The pH of the reaction mixture was adjusted to 8.5–9.0 during conjugation and the clear solution stirred at 5° overnight. The resulting conjugate was dialyzed against carbonate buffer (4 liters, pH9, 0.05 M) and then passed through Sephadex G-25 (medium, carbonate buffer pH9, 0.05 M). The protein fractions were combined and dialyzed against 5×4 l. NH$_4$OH-H$_2$O and then lyophilized to yield 232 mg protein conjugate of hapten number 17 (determined from UV).

c. The NHS ester of 3-(γ-carboxypropyl)amitriptyline (0.9 ml in DMF, from 42.5 mg acid, 0.106 mmole) was added dropwise at 0° to a solution of bovine γ-globulin (BgG, 250 mg, 0.114 mmole lysine) in a mixture of carbonate buffer (12.5 ml, pH9, 0.05 M) and N,N-dimethylformamide (3.5 ml) for a period of 0.5 hr with constant adjustment of pH to 8.5–9.0. The cloudy reaction mixture was allowed to stir at 0° overnight. The resulting milky conjugate was then dialyzed against 1×4 l. carbonate buffer (pH9.65, 0.05 M) for an hour. Afterwards, the pH of the conjugate was adjusted to 10 and the suspension was centrifuged at 5 K for 5 minutes at 0°. The supernatant was passed through Sephadex G-25 (carbonate buffer, pH9.62) and the protein fractions were combined and dialyzed against 5×4 l. $NH_4OH$—$H_2O$ (pH9.6). The resulting conjugate was lyophilized to yield 105 mg protein of hapten number 22 (determined by UV).

EXAMPLE 7

Conjugation of 2- and 3-(γ-Carboxypropyl)amitriptyline to BgG and BSA a. To 2- and 3-(γ-carboxypropyl)amitriptyline HCl (65.6 mg, 0.16 mmole) in N,N-dimethylformamide (1.5 ml) was added triethylamine (22 μl, 0.16 mmole) N-hydroxy succinimide (18.4 mg, 0.16 mmole) and EDAC (35.1 mg, 0.18 mmole) under nitrogen at 5°. The reaction mixture was allowed to stir at 5° overnight.

The NHS ester of 2- and 3-(γ-carboxypropyl)amitriptyline was added slowly at 0°–5° to a clear solution of BgG (500 mg) in a mixture of carbonate buffer (20 ml, 0.05 M, pH9) and N,N-dimethylformamide (7 ml) over a period of 40 min. with constant adjustment of pH to 8.5–9.0. The conjugate was then stirred overnight at 5° and then dialyzed against 1×4 liter carbonate buffer (pH9, 0.05 M). The pH of the conjugate was then adjusted to 9.8–10 and centrifuged (10 K, 10 min). The supernatant was passed through Sephadex G-25 (pH9.5, 0.05 M carbonate buffer) and the protein fractions were combined and dialyzed against 4×4 liter $NH_4O$-H—$H_2O$. The resulting conjugate was then lyophilized to yield 273 mg protein. The hapten number (14.4) was determined by UV.

b. To a solution of 2- and 3-(γ-carboxypropyl)amitriptyline hydrochloride (257 mg, 0.644 mmole) in N,N-dimethylformamide (3 ml) was added triethylamine (89 μl) EDAC, (141 mg, 0.740 mmole) and N-hydroxy succinimide (74 mg, 0.708 mmole) under nitrogen at 5°. The reaction mixture was allowed to stir at 5° for 18 hrs. The formation of NHS ester was observed on tlc (20% MeOH/$CHCl_3$, silica gel plates).

A portion of the 2- and 3-(γ-carboxypropyl)amitriptyline NHS ester (2.5 ml in DMF, 214 mg, 0.537 mmole) was added slowly to a solution of BSA (500 mg) in a mixture of carbonate buffer (30 ml, pH9, 0.05 M) and N,N-dimethylformamide (7 ml) at 5° with the constant adjustment of pH to 8.5–9.0. The reaction mixture was allowed to stir in the cold room (5°) for 72 hrs.

The cloudy BSA conjugate was dialyzed against 4 liters carbonate buffer (0.05 M, pH9) and then centrifuged at 10 K for 20 minutes. The supernatant was passed through Sephadex G-25 (medium, carbonate buffer 0.05 M, pH9), and the protein fraction was collected and dialyzed against 3×4 l. $NH_4OH$-water. The resulting conjugate was lyophilized to yield 540 mg protein (hapten number 53 by UV).

EXAMPLE 8

Conjugation of (2- and 3-)γ-Carboxypropylamitriptyline to Glucose-6-Phosphate Dehydrogenase Into a reaction flask was introduced 10 mg (25 μmoles) of 2- and 3-(3'-carboxypropyl)amitriptyline, 3.16 mg N-hydroxy succinimide (NHS), 5.52 mg EDAC, 3.4 μl triethylamine and 121.6 μl dimethylformamide (DMF) and the mixture stirred overnight at 4°.

To 0.5 ml G-6-PDH (2.5 mg/ml, 777 IV/mg) was added 20 mg G-6-$PNa_2$, 20 mg NADH, 150 μl of carbitol and the NHS ester prepared above in 3 1 μl aliquots followed by a 0.5 μl aliquot over a period of about 3 hrs while maintaining the pH with 0.1 N NaOH between 8.55–8.77, to provide an amitriptyline-enzyme mole ratio of about 58.3. The reaction mixture was then chromatographed over Sephadex G-50 M (80 ml column) employing 0.05 M carbonate buffer (pH9.6) as eluent, collecting 20 drop fractions with fractions 16–21 pooled to provide a total volume of 8 ml. The max rate as determined by a G-6-PDH assay to be described was ΔOD/min 653.3 (% deactivation 82.8) and % inhibitability using saturating amounts of anti(amitriptyline) varied from 85.3 to 90.8 depending on the source of antibody.

The above procedure was repeated except that only 2.75 μl of the NHS ester was added in two aliquots, 2 μl initially followed by 0.75 μl 100 min later to provide a 53.5 mole ratio of amitriptyline-G-6-PDH. After chromatographing, the conjugate was found to be 47.2% deactivated and 60.8 or 66.4% inhibited depending on the source of anti(amitriptyline).

In order to demonstrate the efficacy of compounds prepared in accordance with the subject invention, the antibodies and the enzyme conjugate were employed in a number of assays for amitriptyline. In carrying out the assay, a Gilford 300 N microsample spectrophotometer is employed with a Thermocuvette with a flow cell. All readings are made at 340 mn. The following solutions are prepared as reagents for use in the assay.

Buffer:
   0.055 M tris-HCl pH 8.1 (RT)
Enzyme Conjugate:
   Buffer
   0.9% NaCl
   1.0% RSA, pH 8.1 (RT)
   Sufficient enzyme conjugate to give a maximum rate of ΔOD equal to 600–900 in the assay medium
Assay buffer:
   Buffer
   0.5% NaCl
   0.01% (v/v Triton X-100, pH8.1 (RT)
Antibody Reagent:
   Buffer
   1.0% RSA,
   G6P(Na) 0.066 M,
   NAD 0.04 M, pH5 (RT)
   Antiamitriptyline optimized for assay
   (All % indicated are w/v g/ml. RSA —rabbit serum albumin).

The protocol employed for carrying out an assay is as follows: A sample, 50 microliters is drawn up into a diluter and dispensed with 250 microliters of the assay buffer into a one milliliter Croan cup. A 50 μl aliquot of the diluted sample is drawn up and dispensed with a 250 μl portion of assay buffer into a second Croan cup. Into the second Croan cup is introduced 50 μl of the antibody reagent with 250 μl of the assay buffer, followed by the addition of 50 μl of the enzyme reagent and 250 μl of the assay buffer. Immediately after the enzyme addition, the entire sample is aspirated into the flow cell. After 10 seconds, a first reading is taken, followed by a second reading, after a 40 second interval. The results are reported as the difference in absorbance×2.667.

| Sample Concentration of Amitriptyline ng/ml | | ΔOD |
|---|---|---|
| 0 | (574)* | — |
| 25 | | 28 |
| 50 | | 60 |
| 100 | | 120 |
| 200 | | 187 |
| 400 | | 229 |
| max rate (881)** | | |

*lowest rate in assay with predetermined amount of antibody
**rate of enzyme in absence of antibody The subject assay provides for a sensitive accurate method for determining amitriptyline in biological fluids such as serum. The subject invention provides reagents specific for amitriptyline, which allows for a substantial range of changes in enzyme activity with change in concentration of amitriptyline. The method is rapid, the protocol is simple and relatively free of technician introduced error and can be performed substantially in the same manner as an enzyme assay.

Although the foregoing invention has been described in some detail by way of illustration and example for purposes of clarity and understanding, it will be obvious that certain changes and modifications may be practiced within the scope of the appended claims.

What is claimed is:

1. Compound of the formula;

wherein:
Ami is of the formula:

X is methylene or carbonyl;
Z is hydrogen, hydroxyl, alkoxy of from 1 to 6 carbon atoms, N-oxy succinimide or p-nitrophenoxy ester; and
R is an aliphatic hydrocarbon linking group of from one to seven carbon atoms having from zero to one site of unsaturation.

2. Compound according to claim 1 and of the formula:

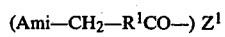

wherein:
Ami is defined in claim 1;
$R^1$ is alkylene of from 1 to 7 carbon atoms;
$Z^1$ is hydrogen, hydroxyl, or alkoxy of from 1 to 6 carbon atoms.

3. Compound according to claim 2, wherein $Z^1$ is hydroxyl.

4. Compound according to claim 2, wherein $Z^1$ is alkoxyl of from 1 to 3 carbon atoms.

5. 3-(γ-carboxypropyl)amitriptyline.
6. 2-(γ-carboxypropyl)amitriptyline.

* * * * *